US008076523B2

(12) United States Patent
Bollmann et al.

(10) Patent No.: US 8,076,523 B2
(45) Date of Patent: Dec. 13, 2011

(54) OLIGOMERISATION IN THE PRESENCE OF BOTH A TETRAMERISATION CATALYST AND A FURTHER OLIGOMERISATION CATALYST

(75) Inventors: Annette Bollmann, Henley-on-Klip (ZA); Hulisani Maumela, Johannesburg (ZA); Kevin Blann, Alberton (ZA)

(73) Assignee: Sasol Technology (PTY) Limited, Johannesburg (ZA)

( * ) Notice: Subject to any disclaimer, the term of this patent is extended or adjusted under 35 U.S.C. 154(b) by 856 days.

(21) Appl. No.: 11/629,785

(22) PCT Filed: Jun. 13, 2005

(86) PCT No.: PCT/IB2005/051941
§ 371 (c)(1),
(2), (4) Date: May 7, 2007

(87) PCT Pub. No.: WO2005/123884
PCT Pub. Date: Dec. 29, 2005

(65) Prior Publication Data
US 2008/0039600 A1    Feb. 14, 2008

(30) Foreign Application Priority Data

Jun. 18, 2004 (ZA) .................................. 2004/4839

(51) Int. Cl.
*C07C 2/08* (2006.01)
(52) U.S. Cl. ........ 585/513; 585/502; 585/520; 585/521; 585/527; 585/522; 585/523; 585/510; 585/511; 585/512
(58) Field of Classification Search .................. 585/513, 585/502, 510, 511, 512, 520, 521, 522, 523, 585/527
See application file for complete search history.

(56) References Cited

U.S. PATENT DOCUMENTS

| | | | |
|---|---|---|---|
| 2,699,457 A | | 1/1955 | Ziegler et al. |
| 5,557,023 A | * | 9/1996 | Somogyvari et al. ......... 585/513 |
| 6,127,301 A | * | 10/2000 | Iwanaga et al. ............... 502/119 |
| 6,521,806 B1 | * | 2/2003 | Tamura et al. ................ 585/512 |
| 6,743,960 B2 | * | 6/2004 | Wang et al. ................... 585/512 |
| 7,297,832 B2 | | 11/2007 | Blann et al. |
| 7,511,183 B2 | | 3/2009 | Blann et al. |
| 2003/0018141 A1 | | 1/2003 | Wass |
| 2003/0166456 A1 | * | 9/2003 | Wass ............................ 502/102 |
| 2004/0059074 A1 | | 3/2004 | Bianchini et al. |

FOREIGN PATENT DOCUMENTS

| | | |
|---|---|---|
| EP | 1 402 949 | 3/2004 |
| WO | WO 03/053890 | 7/2003 |
| WO | WO 03/053891 | 7/2003 |
| WO | WO2004/056478 | 7/2004 |
| WO | WO 2004/056479 | 7/2004 |
| WO | WO 2004/056480 | 7/2004 |

OTHER PUBLICATIONS

Simpson, et. al., "Ethylene Polymers, LLDPE" in Encyclopedia of Polymer Science and Technology, John Wiley, 2002, posted on-line Oct. 22, 2001).*
R. J. Lewis, ed., Hawley's Condensed Chemical Dictionary (14th Edition), John Wiley, 2002, on-line version available at http://knovel.com).*
Lewis, Hawley's Condensed Chemical Dictionary (14th Edition), R. J. Lewis, ed., John Wiley, 2002, on-line version available at http://knovel.com.*
de Wet-Roos, et al., "Homogeneous Tandem Catalysis of Bis(2-decylthioethyl)amine-chromium Trimerization Catalyst in Combination with Metallocene Catalsyts," Macromolecules, 2004, 37, 9314-9320.*
Overett et al., "Ethylene Trimerisation and Tetramerisation Catalysts With Polar-Substituted Diphosphinoamine Ligands", Chem. Commun., 2005, pp. 622-624, (2005).
Bollmann et al., "Ethylene Tetramerization: A New Route to Produce 1-Octene in Exceptionally High Selectivities", J. Am. Chem. Soc., vol. 126, No. 45, pp. 14712-14713, (2004).
Britovsek et al., "Oligomerisation of Ethylene by Bis(Imino)Pyridyliron and -Cobalt Complexes", Chem. Eur. J. vol. 6, No. 12, pp. 2221-2231, (2000).
Overett et al., "Mechanistic Investigations of the Ethylene Tetramerisation Reaction", J. Am. Chem. Soc., vol. 127, No. 30, pp. 10723-10730, (2005).
Tagiyev et al., "Synthesis of Nickel-Organic Complexes Grafted on the Surface of SiO₂ as Catalysts for Ethylene Oligomerization Reaction", Chemical Abstracts Service, 139:53346, 2003, XP-002357441, STN Database Accession No. 1362, 2003:13001 CAPLUS.
Rajanbabu et al., "Heterodimerization of Olefins. 1. Hydrovinylation Reactions of Olefins That Are Amenable to Asymmetric Catalysis", Chemical Abstracts Service, 140:16386, (2003), XP-002357442, STN Database Accession No. 1359, 2003:772364 CAPLUS.
Munshieva, "Study of Di- and Oligomerization of Olefins on Ni(0) Complexes and Heteropolyacids", Chemical Abstracts Service, 141:56010, (2004), XP-002357443, STN Database Accession No. 1356, 2004:252859 CAPLUS.
Deon De Wet-Roos et al., 'HomogeneousTandem Catalysis of Bis(2-decylthioethyl)amine-Chromium Trimerization Catalyst in Combination with Metallocene Catalysts), *Macromolecules* 2004, 37, 9314-9320.
Anthea Carter et al., "High activity ethylene trimerisation catalysts based on diphosphine ligands," *Chem. Commun.*, 2002, 858-859.

* cited by examiner

*Primary Examiner* — In Suk Bullock
*Assistant Examiner* — Bradley Etherton
(74) *Attorney, Agent, or Firm* — Finnegan, Henderson, Farabow, Garrett, & Dunner LLP

(57) ABSTRACT

This invention relates to a process for the oligomerization of at least one olefinic compound in the form of an olefin or a compound including art olefinic moiety by contacting the at least one olefinic compound with at least two different catalysis, namely a tetramerization catalyst and a further oligomerization catalyst. The tetramerization catalyst comprises a combination of a source of a transition metal and a ligating compound of the formula $(R^1)_mX^1(Y)X^2(R^2)_n$. The invention also relates to an oligomerization catalyst comprising the combination of (i) source of transition metal for both a tetramerization catalyst and a trimerization catalyst; (ii) a ligating compound for a tetramerization catalyst: (iii) a different ligating compound for a trimerization catalyst: and (iv) optionally an activator.

26 Claims, No Drawings

OLIGOMERISATION IN THE PRESENCE OF BOTH A TETRAMERISATION CATALYST AND A FURTHER OLIGOMERISATION CATALYST

TECHNICAL FIELD

This invention relates to the oligomerisation of olefinic compounds in the presence of both a tetramerisation catalyst and a further oligomerisation catalyst to produce a mixture of tetramers and other oligomers.

BACKGROUND TO THE INVENTION

Many different processes for the oligomerisation of olefinic compounds are known. The oligomerisation of ethylene and similar processes are described in PCT/ZA2003/000187 which is incorporated herein by reference.

The inventors of the present invention have now found that a tetramerisation reaction as described in PCT/ZA2003/00187 and PCT/ZA2003/000186 (incorporated herein by reference) can be combined with at least one further oligomerisation reaction to yield a mixture of tetramers and other oligomers, wherein the product stream of the tetramerisation reaction contains more than 30% of the tetramer olefin. The processes described in PCT/ZA2003/000187 and PCT/ZA2003/000186 also yield a somewhat mixed oligomerised product, the ratios between the oligomers being dependent on and determined by the catalyst system and reaction conditions selected. The current process can now be used to manipulate the ratios of the oligomers in the product stream as may be required by market needs.

Most surprisingly it has been found that a tetramerisation reaction as described in this patent application is compatible with a further oligomerisation reaction and accordingly is suitable to manipulate the composition of the oligomerised product stream.

DISCLOSURE OF THE INVENTION

According to the present invention there is provided a process for the oligomerisation of at least one olefinic compound in the form of an olefin or a compound including an olefinic moiety by contacting the at least one olefinic compound with at least two different catalysts, namely a tetramerisation catalyst and a further oligomerisation catalyst, wherein the tetramerisation catalyst comprises a combination of
i) a source of a transition metal; and
ii) a ligating compound of the formula

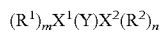
$(R^1)_m X^1(Y)X^2(R^2)_n$ wherein: $X^1$ and $X^2$ are independently selected from the group consisting of N, P, As, Sb, Bi, O, S and Se;
Y is a linking group between $X^1$ and $X^2$;
m and n are independently 0, 1 or a larger integer; and
$R^1$ and $R^2$ are independently hydrogen, a hydrocarbyl group, or a heterohydrocarbyl group, and $R^1$ being the same or different when m>1, and $R^2$ being the same or different when n>1, provided that
(a) if two or more of $R^1$ and $R^2$ are aromatic with a ring atom of the aromatic ring structure bound to either $X^1$ or $X^2$, not more than two of said aromatic $R^1$ and $R^2$ have a substituent as a non-ring atom bound to a ring atom of the aromatic ring structure adjacent to the ring atom bound to $X^1$ or $X^2$; and
(b) none of $R^1$ and $R^2$ are aromatic with a ring atom of the aromatic ring structure bound to either $X^1$ and $X^2$ and with a polar substituent as a non-ring atom bound to a ring atom of the aromatic ring structure adjacent to the ring atom bound to $X^1$ or $X^2$.

In this specification a substituent is a moiety (excluding H) which is bound to a linear structure or a cyclic structure bound to $X^1$ and $X^2$, but does not form part of the linear or cyclic structure.

In this specification a polar substituent is a substituent with a permanent electric or induced dipole moment.

Tetramerisation Catalyst
Source of Transition Metal

Preferably the source of transition metal is a source of a Group IV to VI transition metal. Preferably it is a source of Cr, Ti, V, Ta or Zr. Preferably it is a source of either Cr, Ta or Ti. Most preferably it is a source of Cr.

The source of the Group IV to VI transition metal may be an inorganic salt, an organic salt, a coordination compound or an organometallic complex.

Preferably the source of transition metal is a source of chromium and preferably it is selected from the group consisting of chromium trichloride tris-tetrahydrofuran complex; (benzene)tricarbonyl chromium; chromium (III) octanoate; chromium hexacarbonyl; chromium (III) acetylacetonate and chromium (III) 2-ethylhexanoate. Preferably it is chromium (III) acetylacetonate.

Ligating Compound $X^1$ and/or $X^2$ may be a potential electron donor for coordination with the transition metal.

An electron donor is defined as an entity that donates electrons used in chemical, including dative covalent, bond formation.

$X^1$ and/or $X^2$ may be independently oxidised by S, Se, N or O.

$X^1$ and/or $X^2$ may be independently phosphorus or phosphorus oxidised by S or Se or N or O. Preferably $X^1$ and $X^2$ are the same, and preferably both are P.

It will be appreciated that m and n are dependent on factors such as the valence and oxidation state of $X^1$ and $X^2$, bond formation of Y with $X^1$ and $X^2$ respectively, and bond formation of $R^1$ and $R^2$ with $X^1$ and $X^2$ respectively. Preferably both m an n are not 0.

Preferably the ligating compound is of the formula

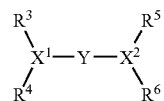

wherein Y is as defined above; $X^1$ and $X^2$ are independently selected from the group consisting of N, P, As, Sb and Bi; and $R^3$ to $R^6$ are the same or different and are each independently a hydrocarbyl group or a heterohydrocarbyl group, provided that
(a) if two or more of $R^3$ to $R^6$ are aromatic with a ring atom of the aromatic ring structure bound to either $X^1$ or $X^2$ not more than two of said aromatic $R^3$ to $R^6$ have a substituent as a non-ring atom bound to a ring atom of the aromatic ring structure adjacent to the ring atom bound to $X^1$ or $X^2$; and
(b) none of $R^3$ to $R^6$ are aromatic with a ring atom of the aromatic ring structure bound to $X^1$ or $X^2$ with a polar substituent as a non-ring atom bound to a ring atom of the aromatic ring structure adjacent to the ring atom bound to $X^1$ or $X^2$.

Preferably $X^1$ and $X^2$ are independently selected from the group consisting of N and P, Preferably $X^1$ and $X^2$ are the same. Preferably both $X^1$ and $X^2$ are P.

One or more of $R^3$ to $R^6$ may be a substituted hydrocarbyl group or a substituted heterohydrocarbyl group, that is at least one substituent is bound to the hydrocarbyl group or the heterohydrocarbyl group. The term "substituent" is as defined earlier, that is a substituent is a moiety (excluding H) which is bound to a linear structure or a cyclic structure bound to $X^1$ or $X^2$, but does not form part of the linear or cyclic structure.

The linear or cyclic structure may be selected from the group consisting of a linear hydrocarbyl, a cyclic hydrocarbyl and a cyclic heterohydrocarbyl group. Linear hydrocarbyl may include ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl and decynyl. Cyclic hydrocarbyl may include cyclopropyl, cyclobutyl, cyclopentyl, cyclohexyl, cycloheptyl cyclooctyl, cyclononyl, cyclodecyl, cyclopentenyl, cyclohexenyl, cyclo-octenyl, phenyl, cyclopentadienyl, naphthaleneyl, norbornyl, adamantyl, phenanthrenyl, anthracenyl, phenalenyl, tetrahydronaphthalenyl, decalinyl, indenyl and tetrahydroindenyl. Cyclic heterohydrocarbyl may include tetrahydrofuranyl, tetrahydrothiophenyl, pyrrolideneyl, piperidinyl, pyrrolinyl, oxazolyl, thiazolyl, furanyl, thiophenyl, pyrazolinyl, pyrazolyl, imidazolyl, benzofuranyl, coumarinyl and indolyl. According to the above definition and for the purpose of clarity, benzyl is considered to be methyl linear structure with a phenyl substituent and tolyl is considered as a phenyl cyclic structure with a methyl substituent.

It will be appreciated that a group such as $H_2ClC—$ is, in terms of this specification considered to be a heterohydrocarbyl group and not a substituted hydrocarbyl group.

$R^3$ to $R^6$ may also be selected from a group of metallocenes such as a ferrocenyl, zirconoceneyl and titanoceneyl group.

In one embodiment of the invention $R^3$ to $R^6$ are the same or different and each is a hydrocarbyl group, or a heterohydrocarbyl group which contains no substituent or contains a non-polar substituent. Preferably each of $R^3$ to $R^6$ does not have any polar substituent. In one embodiment of the invention at least two of (but preferably all of) $R^3$ to $R^6$ are aromatic with a ring atom of the aromatic ring structure bound to $X^1$ or $X^2$, but not more than two of said aromatic $R^3$ to $R^6$ having a non-polar substituent as a non-ring atom bound to a ring atom of the aromatic ring structure adjacent to the ring atom bound to $X^1$ or $X^2$. Preferably none of the aromatic $R^3$ to $R^6$ have a non-polar substituent as a non-ring atom bound to a ring atom of the aromatic ring structure adjacent to the ring atom bound to $X^1$ or $X^2$. Preferably all of aromatic $R^3$ to $R^6$ are non-substituted aromatic compounds. $R^3$ to $R^6$ may be independently selected from the group consisting of a non-aromatic compound; an aromatic compound; and a heteroaromatic compound. Preferably each of $R^3$ to $R^6$ is an aromatic or heteroaromatic compound, more preferably an aromatic compound (including a substituted aromatic compound). The aromatic compound (or substituted aromatic compound) may comprise phenyl or a substituted phenyl.

In this specification a non-polar substituent is a substituent without a permanent electric or induced dipole moment.

Examples of suitable non-polar substituents include, but are not limited to, methyl, ethyl, ethenyl, propyl, iso-propyl, cyclopropyl, propenyl, propynyl, butyl, sec-butyl, tertiary-butyl, cyclobutyl, butenyl, butynyl, pentyl, isopentyl, neopentyl, cyclopentyl, pentenyl, pentynyl, hexyl, sec-hexyl, cyclohexyl, 2-methylcyclohexyl, 2-ethylcyclohexyl, 2-isopropylcyclohexyl, cyclohexenyl, hexenyl, hexynyl, octyl, cyclo-octyl, cyclo-octenyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like.

Any one of $R^3$ to $R^6$ may be independently linked to one or more of each other, or to Y to form a cyclic structure.

In yet another embodiment of the invention $R^3$ to $R^6$ are the same or different and each is a hydrocarbyl group, or a heterohydrocarbyl group, provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$. One or more, or all of $R^3$ to $R^6$ may be independently selected from the group consisting of a substituted non-aromatic compound; a substituted aromatic compound; and a substituted heteroaromatic compound. Preferably each of $R^3$ to $R^6$ is a substituted aromatic or a substituted heteroaromatic compound, more preferably a substituted aromatic compound. The substituted aromatic compound may comprise a substituted phenyl.

Any polar substituent on one or more of $R^3$, $R^4$, $R^5$ and $R^6$ may be electron donating.

Suitable polar substituents may be a methoxy, ethoxy, isopropoxy, $C_3$-$C_{20}$ alkoxy, phenoxy, methoxymethyl, methylthiomethyl, 1,3-oxazolyl, methoxymethoxy, hydroxyl, amino, pentafluorophenoxy, tosyl, methylsulfanyl, trimethylsiloxy, dimethylamino, sulphate, nitro or the like.

$R^3$ and $R^4$ may be the same, and $R^5$ and $R^6$ may be the same. $R^3$ to $R^6$ may all be the same.

Y may be selected from the group consisting of an organic linking group such as a hydrocarbyl, a substituted hydrocarbyl, a heterohydrocarbyl and a substituted heterohydrocarbyl; an inorganic linking group such as a single atom link (that is $X^1$ and $X^2$ are bound to the same atom); methylene; dimethylmethylene; 1,2-ethane; 1,2-ethene; 1,1-cyclopropane; 1,1-cyclobutane; 1,1-cyclohexane; 1,1-cyclopentane; 1,2-cyclopentane; 1,2-cyclohexane; 1,2-phenylene; 1,8-naphthyl; 9,10-phenanthrene; 4,5-phenanthrene; 1,3-propane; 1,2-catechol; 1,2-diallylhydrazine; $—B(R^7)—$, $—Si(R^7)_2—$, $—P(R^7)—$ and $—N(R^7)—$ where $R^7$ is hydrogen, a hydrocarbyl or heterohydrocarbyl or halogen. Preferably, Y may be $—N(R^7)—$ and $R^7$ may be selected from the group consisting of hydrogen, alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. Preferably $R^7$ may be a hydrocarbyl or a substituted hydrocarbyl group. $R^7$ may be methyl, ethyl, propyl, isopropyl, cyclopropyl, allyl, butyl, tertiary-butyl, sec-butyl, cyclobutyl, pentyl, isopentyl, neopentyl, cyclopentyl, cyclohexyl, cycloheptyl, cyclo-octyl, decyl, cyclodecyl, 1,5-dimethylheptyl, 2-naphthylethyl, 1-naphthylmethyl, adamantylmethyl, adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, isopinocamphenyl, dimethylamino, phthalimido, pyrrolyl, trimethylsilyl, dimethyl-tertiary-butylsilyl, 3-trimethoxysilane-propyl, indanyl, cyclohexanemethyl, 2-methoxyphenyl, 3-methoxyphenyl, 4-methoxyphenyl, 4-tertiary-butylphenyl, 4-nitrophenyl, (1,1'-bis(cyclohexyl)-4,4'-methylene), 1,6-hexylene, 1-naphthyl, 2-naphthyl, N-morpholine, diphenylmethyl, 1,2-diphenyl-ethyl, phenylethyl, 2-methylphenyl, 3-methylphenyl, 4-methylphenyl, 2,6-dimethyl-phenyl, 1,2,3,4-tetrahydronaphthyl, or a 2-octyl group.

Y may exclude $(CH_2)_xZ(CH_2)_y$, where Z is —$P(R^8)$—, —$N(R^8)$—, —$As(R^8)$—, —$Sb(R^8)$— or —S— and x and y are individually 1-15 and wherein $R^8$ is hydrogen or a halogen or a nitro group or a hydrocarbyl or a substituted hydrocarbyl group.

Y may include a first atom bound to $X^1$ and a different atom bound to $X^2$. Preferably Y includes or is a single atom bound to both $X^1$ and $X^2$.

Preferably the ligating compound is of the formula

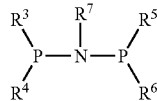

with $R^3$ to $R^7$ as defined above.

Preferably, the ligating compound is a bidentate ligand.

Non limiting examples of the ligating compound are (phenyl)$_2$PN(methyl)P(phenyl)$_2$; (phenyl)$_2$PN(ethyl)P(phenyl)$_2$; (phenyl)$_2$PN(propyl)P(phenyl)$_2$; (phenyl)$_2$PN(butyl)P(phenyl)$_2$; (phenyl)$_2$PN(pentyl)P(phenyl)$_2$; (phenyl)$_2$PN(hexyl)P(phenyl)$_2$; (phenyl)$_2$PN(heptyl)P(phenyl)$_2$; (phenyl)$_2$PN(octyl)P(phenyl)$_2$; (phenyl)$_2$PN(nonyl)P(phenyl)$_2$; (phenyl)$_2$PN(decyl)P(phenyl)$_2$; (phenyl)$_2$PN(cyclopropyl)P(phenyl)$_2$; (phenyl)$_2$PN(cyclobutyl)P(phenyl)$_2$; (phenyl)$_2$PN(cyclopentyl)P(phenyl)$_2$; (phenyl)$_2$PN(cyclohexyl)P(phenyl)$_2$; (phenyl)$_2$PN(cycloheptyl)P(phenyl)$_2$; (phenyl)$_2$PN(cyclooctyl)P(phenyl)$_2$; (phenyl)$_2$PN(cyclodecyl)P(phenyl)$_2$; (phenyl)$_2$PN(cyclododecyl)P(phenyl)$_2$; (phenyl)$_2$PN(isopropyl)P(phenyl)$_2$; (phenyl)$_2$PN(isobutyl)P(phenyl)$_2$; (phenyl)$_2$PN(secbutyl)P(phenyl)$_2$; (phenyl)$_2$PN(tertiarybutyl)P(phenyl)$_2$; (phenyl)$_2$PN(neopentyl)P(phenyl)$_2$; (phenyl)$_2$PN(1,2-dimethyl-propyl)P(phenyl)$_2$; (phenyl)$_2$PN(allyl)P(phenyl)$_2$; (phenyl)$_2$PN(methylheptyl)P(phenyl)$_2$; (phenyl)$_2$PN(1,5-dimethyl-heptyl)P(phenyl)$_2$; (phenyl)$_2$PN(2-ethylhexyl)P(phenyl)$_2$; (phenyl)$_2$PN(3-trimethoxysilane-propyl)P(phenyl)$_2$; (phenyl)$_2$PN(indanyl)P(phenyl)$_2$; (phenyl)$_2$PN(cyclohexylethyl)P(phenyl)$_2$; (phenyl)$_2$PN(2-methylcyclohexyl)P(phenyl)$_2$; (phenyl)$_2$PN(adamantyl)P(phenyl)$_2$; (phenyl)$_2$PN(adamantylmethyl)P(phenyl)$_2$; (phenyl)$_2$PN(cyclohexanemethyl)P(phenyl)$_2$; (phenyl)$_2$PN(benzyl)P(phenyl)$_2$; (phenyl)$_2$PN(phenyl)P(phenyl)$_2$; (phenyl)$_2$PN((4-methoxy)-phenyl)P(phenyl)$_2$; (phenyl)$_2$PN((3-methoxy)-phenyl)P(phenyl)$_2$; (phenyl)$_2$PN((2-methoxy)phenyl)P(phenyl)$_2$; (phenyl)$_2$PN((4-t-butyl)-phenyl)P(phenyl)$_2$; (phenyl)$_2$PN((4-nitro)-phenyl)P(phenyl)$_2$; (phenyl)$_2$PN(1-naphthyl)P(phenyl)$_2$; (phenyl)$_2$PN(2-naphthyl)P(phenyl)$_2$; (phenyl)$_2$PN(4-pyridyl)P(phenyl)$_2$ (phenyl)$_2$ PN(3-(N-morpholine)-propyl)P(phenyl)$_2$; (phenyl)$_2$PN(2-naphtyl-ethyl)P(phenyl)$_2$; (phenyl)$_2$PN(1-naphtylmethyl)P(phenyl)$_2$; (phenyl)$_2$PN(diphenylmethyl)P(phenyl)$_2$; (phenyl)$_2$PN (1,2-diphenyl-ethyl)P(phenyl)$_2$; (phenyl)$_2$PN(phenylethyl)P(phenyl)$_2$; (phenyl)$_2$PN((2-methyl)phenyl)P(phenyl)$_2$; (phenyl)$_2$PN((3-methyl)phenyl)P(phenyl)$_2$; (phenyl)$_2$PN((4-methyl)phenyl)P(phenyl)$_2$; (phenyl)$_2$PN((2,6-dimethyl)phenyl)P(phenyl)$_2$; (phenyl)$_2$PN((2-ethyl)-phenyl)P(phenyl)$_2$; (phenyl)$_2$PN (1,2,3,4-Tetrahydronaphthyl)P(phenyl)$_2$; (phenyl)$_2$PN((2-methyl)cyclohexyl)P(phenyl)$_2$; (phenyl)$_2$PN((3-methyl)cyclohexyl)P(phenyl)$_2$; (phenyl)$_2$PN((4-methyl)cyclohexyl)P(phenyl)$_2$; (phenyl)$_2$PN((2-ethyl)cyclohexyl)P(phenyl)$_2$; (phenyl)$_2$PN((2-isopropyl)cyclohexyl)P(phenyl)$_2$; (phenyl)$_2$PN((2,6-dimethyl)cyclohexyl)P(phenyl)$_2$; (phenyl)$_2$PN(exo-2-nonorbornanyl)P(phenyl)$_2$; (phenyl)$_2$PN(isopinocampheyl)P(phenyl)$_2$; (phenyl)$_2$PN(dimethylamino)P(phenyl)$_2$; (phenyl)$_2$PN(phthalimido)P(phenyl)$_2$; (phenyl)$_2$PN(pyrrolyl)P(phenyl)$_2$; (phenyl)$_2$PN(trimethylsilyl)P(phenyl)$_2$; (phenyl)$_2$PN(dimethyltertiarybutylsilyl)P(phenyl)$_2$; [(phenyl)$_2$P]$_2$N(1,1'-bis (cyclohexyl)-4,4'-methylene))N[P(phenyl)$_2$]$_2$; ([(phenyl)$_2$P]$_2$ N(1,6-hexylene-)N[P(phenyl)$_2$]$_2$; (2,2',2"-trimethylamino)[N[P(phenyl)$_2$]$_2$]$_3$; (4-biphenyl)PN(methyl)P(4-biphenyl)$_2$; (2-naphthyl)$_2$PN(methyl)P(2-naphthyl)$_2$; (4-methylphenyl)$_2$ PN(methyl)P(4-methylphenyl)$_2$; (3-methylphenyl)$_2$PN(methyl)P(3-methylphenyl)$_2$; (2-naphthyl)$_2$PN(methyl)P(phenyl)$_2$; (2-naphthyl)(phenyl)PN(methyl)P(2-naphthyl)(phenyl); (2-naphthyl)$_2$PN(methyl)P(2-naphthyl)(phenyl); (2-naphthyl)(phenyl)PN(methyl)P (phenyl)$_2$; (2-methylphenyl)(phenyl)PN(isopropyl)P(2-methylphenyl)(phenyl); (2-methylphenyl)$_2$PN(methyl)P (phenyl)$_2$; (2-methylphenyl)(phenyl)PN(isopropyl)P (phenyl)$_2$; (ethyl)$_2$PN(methyl)P(ethyl)$_2$; (ethyl)$_2$PN (isopropyl)P(ethyl)$_2$; (ethyl)$_2$PN(tertiarybutyl)P(ethyl)$_2$; (methyl)$_2$PN(isopropyl)P(methyl)$_2$; (isopropyl)$_2$PN(methyl) P(isopropyl)$_2$; (ethyl)$_2$PN(isopropyl)P(ethyl)(phenyl); (ethyl)(phenyl)PN(isopropyl)P(ethyl)(phenyl); (ethyl)$_2$PN(isopropyl)P(phenyl)$_2$; (ethyl)(phenyl)PN(isopropyl) P(phenyl)$_2$; (2-thiophenyl)$_2$PN(isopropyl)P(2-thiophenyl)$_2$; (diphenylphosphinite)N(isopropyl)(diphenylphosphinite); (dibenzothiaphosphonine)N(isopropyl)(dibenzothiaphosphonine); (dibenzooxaphosphonine)N(isopropyl)(dibenzooxaphosphonine); (phenyl)$_2$PN(methyl)N(methyl)P(phenyl)$_2$; (phenyl)$_2$PN(ethyl)N(ethyl)P(phenyl)$_2$; (phenyl)$_2$PN (phenyl)N(phenyl)P(phenyl)$_2$; (phenyl)$_2$PN(isopropyl)N (isopropyl)P(phenyl)$_2$; (phenyl)$_2$PN(isopropyl)N(methyl)P (phenyl)$_2$; (phenyl)$_2$PN(isopropyl)N(methyl) P(phenyl)$_2$; (4-methylphenyl)$_2$P—N(CH$_3$)N(CH$_3$)—P(4-methylphenyl)$_2$; (3-methylphenyl)$_2$P—N(CH$_3$)N(CH$_3$)—P (3-methylphenyl)$_2$; (2-methylphenyl)$_2$P—N(CH$_3$)N (CH$_3$)—P(phenyl)$_2$; (ethyl)$_2$P—N(CH$_3$)N(CH$_3$)—P(ethyl)$_2$; (methyl)$_2$P—N(CH$_3$)N(CH$_3$)—P(methyl)$_2$; (isopropyl)$_2$P—N(CH$_3$)N(CH$_3$)—P(isopropyl)$_2$; (ethyl)$_2$P—N (CH$_3$)N(CH$_3$)—P(ethyl)(phenyl); (ethyl)(phenyl)P—N (CH$_3$)N(CH$_3$)—P(ethyl)(phenyl); (ethyl)$_2$P—N(CH$_3$)N (CH$_3$)—P(Phenyl)$_2$; (ethyl)(phenyl)P—N(CH$_3$)—P (phenyl)$_2$; (2-thiophenyl)$_2$P—N(CH$_3$)N(CH$_3$)—P(2-thiophenyl)$_2$; (2-naphthyl)$_2$P—N(CH$_3$)N(CH$_3$)—P(2-naphthyl)$_2$; (4-biphenyl)$_2$P—N(CH$_3$)N(CH$_3$)—P(4-biphenyl)$_2$; (phenyl)$_2$P-1,8-naphthyl-P(phenyl)$_2$; (phenyl)$_2$P-9,10-phenanthrene-P(phenyl)$_2$; (phenyl)$_2$P-4,5-phenananthrene-P(phenyl)$_2$; (phenyl)$_2$P—C(CH$_3$)$_2$—P (phenyl)$_2$; (phenyl)$_2$P—C(CH$_2$)$_2$—P(phenyl)$_2$; (phenyl)$_2$P-1,2-benzene-P(phenyl)$_2$; (4-methylphenyl)$_2$P-1,2-benzene-P (4-methylphenyl)$_2$; (3-methylphenyl)$_2$P-1,2-benzene-P(3-methylphenyl)$_2$; (2-methylphenyl)$_2$P-1,2-benzene-P (phenyl)$_2$; (ethyl)$_2$P-1,2-benzene-P(ethyl)$_2$; (methyl)$_2$P-1,2-benzene-P(methyl)$_2$; (isopropyl)$_2$P-1,2-benzene-P (isopropyl)$_2$; (ethyl)$_2$P-1,2-benzene-P(ethyl)(phenyl); (ethyl)(phenyl)P-1,2-benzene-P(ethyl)(phenyl); (ethyl)$_2$P-1,2-benzene-P(phenyl)$_2$; (ethyl)(phenyl)P-1,2-benzene-P(phenyl)$_2$; (2-thiophenyl)$_2$P-1,2-benzene-P(2-thiophenyl)$_2$; (2-naphthyl)$_2$P-1,2-benzene-P(2-naphthyl)$_2$; (4-biphenyl)$_2$ P-1,2-benzene-P(4-biphenyl)$_2$; (phenyl)$_2$P—CH$_2$CH$_2$—P(phenyl)$_2$; (4-methylphenyl)$_2$P—CH$_2$CH$_2$—P(4-methylphenyl)$_2$; (3-methylphenyl)$_2$P—CH$_2$CH$_2$—P(3-methylphenyl)$_2$; (4-methylphenyl)$_2$P—CH$_2$CH$_2$—P(4-methylphenyl)(phenyl); (4-methylphenyl)(phenyl)P—CH$_2$CH$_2$—P(4-methylphenyl)(phenyl); (4-methylphenyl)$_2$P—CH$_2$CH$_2$—P(phenyl)$_2$; (4-methylphenyl)(phenyl)P—CH$_2$CH$_2$—P(phenyl)$_2$; (2-methylphenyl)$_2$P—CH$_2$CH$_2$—P (phenyl)$_2$; (ethyl)$_2$P—CH$_2$CH$_2$—P(ethyl)$_2$; (methyl)$_2$P—CH$_2$CH$_2$—P(methyl)$_2$; (isopropyl)$_2$P—CH$_2$CH$_2$—P (isopropyl)$_2$; (ethyl)$_2$P—CH$_2$CH$_2$—P(ethyl)(phenyl); (ethyl)(phenyl)P—CH$_2$CH$_2$—P(ethyl)(phenyl); (ethyl)$_2$P—CH$_2$CH$_2$—P(phenyl)$_2$; (ethyl)(phenyl)P—CH$_2$CH$_2$—P (phenyl)$_2$; (2-thiophenyl)$_2$P—CH$_2$CH$_2$—P(2-thiophenyl)$_2$; (phenyl)$_2$PB(phenyl)P(phenyl)$_2$; (phenyl)$_2$PP(phenyl)P (phenyl)$_2$; (phenyl)$_2$PSi(methyl)$_2$P(phenyl)$_2$; (phenyl)$_2$AsN(isopropyl)As(phenyl)$_2$; (phenyl)SN(isopropyl)S(phenyl); (phenyl)$_2$PN(isopropyl)S(phenyl); (phenyl)$_2$PN(isopropyl)As(phenyl)$_2$; (phenyl)$_2$PN (isopropyl) P(=O)(Phenyl)$_2$; (phenyl)$_2$P(=O)N(isopropyl)P(=O)(phenyl)$_2$; (phenyl)$_2$PN(isopropyl)P(=S)(phenyl)$_2$; (Phenyl)$_2$P(=S)N(isopropyl)P(=S)(phenyl)$_2$; (phenyl)$_2$P(=O)N(isopropyl)P(=S)(phenyl)$_2$; (4-trifluoromethylphenyl)$_2$PN(isopropyl)P(4-trifluoromethylphenyl)$_2$; (4-chlorophenyl)$_2$PN(isopropyl)P(4-chlorophenyl)$_2$; (4-methoxyphenyl)$_2$PN(methyl)P(4-methoxyphenyl)$_2$; (4-methoxyphenyl)$_2$PN(isopropyl)P(4-methoxyphenyl)$_2$; (3-methoxyphenyl)$_2$PN(methyl)P(3-methoxyphenyl)$_2$; (4-methoxyphenyl)$_2$PN(isopropyl)P(4-methoxyphenyl)(phenyl); (4-methoxyphenyl)(phenyl)PN(isopropyl)P(4-methoxyphenyl)(phenyl); (4-methoxyphenyl)$_2$PN(isopropyl)P(phenyl)$_2$; (4-methoxyphenyl)(phenyl)PN(isopropyl)P(phenyl)$_2$; (4-methoxyphenyl)$_2$P—N(CH$_3$)N(CH$_3$)—P(4-methoxyphenyl)$_2$; (3-methoxyphenyl)$_2$P—N(CH$_3$)N(CH$_3$)—P(3-methoxyphenyl)$_2$; (4-methoxyphenyl)$_2$P—N(CH$_3$)N(CH$_3$)—P(4-methoxyphenyl)(phenyl); (4-methoxyphenyl)(phenyl)P—N(CH$_3$)N(CH$_3$)—P(4-methoxyphenyl)(phenyl); (4-methoxyphenyl)$_2$P—N(CH$_3$)N(CH$_3$)—P(phenyl)$_2$; (4-methoxyphenyl)(phenyl)P—N(CH$_3$)N(CH$_3$)—P(phenyl)$_2$; (4-methoxyphenyl)$_2$P-1,2-benzene-P(4-methoxyphenyl)$_2$; (3-methoxyphenyl)$_2$P-1,2-benzene-P(3-methoxyphenyl)$_2$; (4-methoxyphenyl)$_2$P-1,2-benzene-P(4-methoxyphenyl)(phenyl); (4-methoxyphenyl)(phenyl)P-1,2-benzene-P(4-methoxyphenyl)(phenyl); (4-methoxyphenyl)$_2$P-1,2-benzene-P(phenyl)$_2$; (4-methoxyphenyl)(phenyl)P-1,2-benzene-P(phenyl)$_2$; (3-methoxyphenyl)$_2$P(CH$_2$CH$_2$)P(3-methoxyphenyl)$_2$; (3-methoxyphenyl)$_2$P(CH$_2$CH$_2$)P(3-methoxyphenyl)(phenyl); (3-methoxyphenyl)(phenyl)P(CH$_2$CH$_2$CH$_2$)P(3-methoxyphenyl)(phenyl); (3-methoxyphenyl)(phenyl)P(CH$_2$CH$_2$)P(3-methoxyphenyl)(phenyl); (3-methoxyphenyl)(phenyl)P(CH$_2$)P(3-methoxyphenyl)(phenyl); (3-methoxyphenyl)$_2$P(CH$_2$CH$_2$)P(phenyl)$_2$; (3-methoxyphenyl)(phenyl)P(CH$_2$CH$_2$)P(phenyl)$_2$; (4-methoxyphenyl)$_2$P(CH$_2$CH$_2$)P(4-methoxyphenyl)$_2$; (4-methoxyphenyl)$_2$P(CH$_2$CH$_2$)P(4-methoxyphenyl)(phenyl); (4-methoxyphenyl)(phenyl)P(CH$_2$CH$_2$CH$_2$)P(4-methoxyphenyl)(phenyl); (4-methoxyphenyl)(phenyl)P(CH$_2$CH$_2$)P(4-methoxyphenyl)(phenyl); (4-methoxyphenyl)(phenyl)P(CH$_2$)P(4-methoxyphenyl)(phenyl); (4-methoxyphenyl)$_2$P(CH$_2$CH$_2$)P(phenyl)$_2$ and (4-methoxyphenyl)(phenyl)P(CH$_2$CH$_2$)P(phenyl)$_2$.

The ligating compound may include a polymeric moiety to render the reaction product of the source of transition metal and the said ligating compound to be soluble at higher temperatures and insoluble at lower temperatures e.g. 25° C.

This approach may enable the recovery of the complex from the reaction mixture for reuse and has been used for other catalyst as described by D. E. Bergbreiter et al., *J. Am. Chem. Soc.*, 1987, 109, 177-179. In a similar vein these transition metal catalysts can also be immobilised by binding the ligating compound to silica, silica gel, polysiloxane or alumina backbone as, for example, demonstrated by C. Yuanyin et al., *Chinese J. React. Pol.*, 1992, 1(2), 152-159 for immobilising platinum complexes.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P(phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N(methyl)P(p-methoxyphenyl)$_2$)-benzene.

The ligating compounds may be prepared using procedures known to one skilled in the art and procedures forming part of the state of the art.

The tetramerisation catalyst may be prepared in situ, that is in the reaction mixture in which the oligomerisation reaction is to take place. Reaction mixture will be understood to include a reaction medium, reactants (olefinic compounds), reaction products and catalyst components. Typically the oligomerisation catalyst will be prepared in situ. However it is foreseen that the catalyst may be pre-formed or partly pre-formed.

The source of transition metal and ligating compound may be combined (in situ or ex situ) to provide any suitable molar ratio, preferably a transition metal to ligand compound molar ratio, from about 0.01:100 to 10 000:1, preferably from about 0.1:1 to 10:1.

The process may also include combining one or more different sources of transition metal with one or more different ligating compounds.

The tetramerisation catalyst or its individual components, in accordance with the invention, may also be immobilised by supporting it on a support material, for example, silica, alumina, MgCl$_2$, zirconia, artificial hectorite or smectorite clays such as Laponite™ RD or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components or the oligomerisation catalyst. In some cases, the support material can also act as a component of the activator. This approach would also facilitate the recovery of the catalyst from the reaction mixture for reuse.

Activation

The catalyst may also include one or more activators. Such an activator may be a compound that generates an active catalyst when the activator is combined with the source of transition metal and the ligating compound.

Suitable activators include aluminium compounds (including organoaluminum compounds), organoboron compounds, organic salts such as methyllithium and methylmagnesium bromide, inorganic acids and salts such as tetrafluoroboric acid etherate, silver tetrafluoroborate, sodium hexafluoroantimonate, and the like. Suitable aluminium compounds include compounds of the formula Al(R$^9$)$_3$ (R$^9$ being the same or different), where each R$^9$ is independently a C$_1$-C$_{12}$ alkyl, an oxygen containing moiety or a halide, aluminoxanes, and compounds such as LiAlH$_4$ and the like. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Examples of suitable organoaluminium activators include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), isobutylaluminoxane (iBuAO), modified alkylaluminoxanes such as modified methylaluminoxane (MMAO) and mixture thereof.

Examples of suitable organoboron compounds are boroxines, NaBH$_4$, triethylborane, tris(pentafluorophenyl)borane, trityl tetrakis(pentafluorophenyl) borate, dimethylaniliumtetrakis(pentafluorophenyl)borate, tributyl borate and the like.

The activator may also be or contain a compound that acts as a reducing or oxidising agent, such as sodium or zinc metal and the like, or hydrogen or oxygen and the like.

The activator may be selected from alkylaluminoxanes such as methylaluminoxane (MAO), high stability methylaluminoxane (MAO HS), ethylaluminoxane (EAO), isobutylaluminoxane (iBuAO) well as modified alkylaluminoxanes such as modified methylaluminoxane (MMAO). Modified methylaluminoxane (a commercial product from Akzo-Nobel) contains modifier groups such as isobutyl or n-octyl groups, in addition to methyl groups.

The transition metal source and the aluminoxane may be combined in proportions to provide Al/transition metal molar ratios from about 1:1 to 10 000:1, preferably from about 1:1 to 1000:1, and more preferably from 1:1 to 500:1.

The process may include the step of adding to the catalyst system a trialkylaluminium compound in amounts of between 0.01 to 1000 mol per mol of alkylaluminoxane.

It should be noted that aluminoxanes generally also contain considerable quantities of the corresponding trialkylaluminium compounds used in their preparation. The presence of these trialkylaluminium compounds in aluminoxanes can be attributed to their incomplete hydrolysis with water. Any quantity of a trialkylaluminium compound quoted in this disclosure is additional to alkylaluminium compounds contained within the aluminoxanes.

Further Oligomerisation Catalyst

The further oligomerisation catalyst may comprise a conventional oligomerisation catalyst (e.g. as described in U.S. Pat. No. 6,555,723, U.S. Pat. No. 6,683,187 and US 20030144514), a dimerisation catalyst (e.g. as described in US 2003/0149198), but preferably it comprises a trimerisation catalyst. Preferably it comprises a trimerisation catalyst as described in any one of U.S. Pat. No. 5,811,618, WO 02/04119, WO 03/053890, WO 03/053891 and PCT/ZA2003/000185, all of which are incorporated herein by reference. Preferably it comprises a catalyst as described in WO 03/053890 or PCT PCT/ZA2003/000185.

Tetramerisation Catalyst and Further Oligomerisation Catalyst

In a preferred embodiment of the invention the further oligomerisation catalyst is a catalyst comprising the combination of
i) a source of transition metal; and
ii) a ligating compound, preferably of the formula

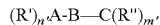

where
A and C are independently selected from the group consisting of N, P, As, Sb, Bi, O, S and Se;
B is a linking group between A and C;
m' and n' are independently 0, 1 or a larger integer;
R' and R" are independently hydrogen, a hydrocarbyl group or a heterohydrocarbyl group;
and R' being the same or different when n≧1, and R" being the same or different when n≧1.

Preferably the oligomerisation catalyst is a trimerisation catalyst and the source of transition metal and ligating compound is as described in U.S. Pat. No. 5,811,618, WO 02/04119, WO/053890 or WO 03/053891 or PCT/ZA2003/000185, all of which are incorporated herein by reference.

Preferably the source of transition metal of the tetramerisation catalyst and the further oligomerisation catalyst as described above is the same source. Preferably it is a source of Cr in both cases.

In one embodiment of the invention both the tetramerisation catalyst and the further oligomerisation catalyst may be prepared in the same medium (preferably in situ). The preparation may be carried out by combining
i) a source of transition metal for both the tetramerisation catalyst and the further oligomerisation catalyst;
ii) a ligating compound for the tetramerisation catalyst as defined above;
iii) a different ligating compound for the oligomerisation (preferably trimerisation) catalyst; and
iv) optionally an activator.

The oligomerisation catalyst, may be a trimerisation catalyst, and preferably it is as described in U.S. Pat. No. 5,811, 618, WO 02/04119, WO/053890 or WO 03/053891 or PCT/ZA2003/000185.

The molar ratio of the ligating compound for the tetramerisation catalyst to the ligating compound for the other oligomerisation catalyst may be varied as required and may for example be 0.05:1 or 1:1 or 1:2 or 1:3.

According to another aspect of the present invention there is provided an oligomerisation catalyst comprising the combination of
i) source of transition metal for both a tetramerisation catalyst and a trimerisation catalyst;
ii) a ligating compound for a tetramerisation catalyst as defined above;
iii) a different ligating compound for a trimerisation catalyst; and
iv) optionally an activator.

Oligomeric Product

The oligomeric product may include a mixture of at least one tetramer and at least one other oligomer. Both the at least one tetramer and the at least one other oligomer may comprise olefins or compounds including an olefinic moiety. Preferably both are olefins, preferably olefins containing a single carbon-carbon double bond, and preferably both comprise α-olefins. The at least one tetramer may comprise octene, preferably 1-octene. The at least one other oligomer may comprise a trimer, preferably hexene, preferably 1-hexene.

The at least one tetramer and the at least one other oligomer may be branched, but preferably they are non-branched.

Olefinic Compound

The at least one olefinic compound may comprise a single olefinic compound or mixture at olefinic compounds. In one embodiment of the invention it may comprise a single olefin.

The at least one olefinic compound preferably comprises an olefin and the olefin may include multiple carbon-carbon double bonds, but preferably it comprises a single carbon-carbon double bond. The olefin may comprise an α-olefin with 2 to 30 carbon atoms, preferably 2 to 10 carbon atoms. The olefinic compound may be selected from the group consisting of ethene, propene, 1-butene, 1-pentene, 1-hexene, styrene, 1-heptene, and 1-octene, 1-nonene, 1-decene, 3-methyl-1-butene, 3-methyl-1-pentene, 4-methyl-1-pentene, p-methyl styrene, 1-dodecene or combinations thereof. Preferably it comprises ethene or propene, preferably ethene. The ethene may be used to produce octene (preferably 1-octene) and other oligomers, preferably hexene (preferably 1-hexene).

Process

The molar ratio of the tetrameristaion catalyst to the further oligomerisation catalyst may be 0.01:1 to 100:1, preferably 0.1:1 to 10:1.

The olefinic compound or mixture thereof to be oligomerised according to this invention can be introduced into the process in a continuous or batch fashion.

The olefinic compound or mixture of olefinic compounds may be contacted with the oligomerisation catalysts at a pressure of 100 kPa or higher, preferably greater than 1000 kPa, more preferably greater than 3000 kPa. Preferred pressure ranges are from 1000 to 30000 kPa, more preferably from 3000 to 10000 kPa.

The process may be carried out at temperatures from −100° C. to 250° C. Temperatures in the range of 15-150° C. are preferred. Particularly preferred temperatures range from 40-120° C.

The oligomerisation process may include the step of mixing the components of the catalysts at any temperature between −20° C. and 250° C. in the presence or absence of an olefinic compound or mixture thereof. The preferred temperature range being from 20° C. to 150° C. The components of the catalysts may also be added separately and at different temperatures to allow for selective and controlled contact between the components.

The individual components constituting the tetramerisation catalyst or further oligomerisation catalyst described herein may be combined simultaneously or sequentially in any order, and in the presence or absence of a solvent, in order to give an active and selective catalyst. The presence of an olefinic compound during the mixing of the catalyst components generally provides a protective effect which may result in improved catalyst performance.

The reaction products derived from the oligomerisation reaction as described herein, may be prepared using the disclosed catalysts by a homogeneous liquid phase reaction in the presence or absence of an inert solvent, and/or by slurry reaction where the catalysts and the oligomeric product is in a form that displays little or no solubility, and/or a two-phase liquid/liquid reaction, and/or a bulk phase reaction in which neat reagent and/or product olefins serve as the dominant medium, and/or gas phase reaction, using conventional equipment and contacting techniques.

The oligomerisation reaction may also be carried out in an inert solvent. Any inert solvent that does not react with the activator can be used. These inert solvents may include any saturated aliphatic and unsaturated aliphatic and aromatic hydrocarbon and halogenated hydrocarbon. Typical solvents include, but are not limited to, benzene, toluene, xylene, cumene, heptane, methylcyclohexane, methylcyclopentane, cyclohexane, Isopar C, ionic liquids as well as the product formed during the reaction in a liquid state and the like.

The oligomerisation reaction may be carried out in a plant which includes reactor types known in the art. Examples of such reactors include, but are not limited to, batch reactors, semi-batch reactors and continuous reactors. The plant may include, in combination a) a stirred or fluidised bed reactor system, b) at least one inlet line into this reactor for olefin reactant and the catalyst system, c) effluent lines from this reactor for oligomerisation reaction products, and d) at least one separator to separate the desired oligomerisation reaction products which may include a recycle loop for solvents and/or reactants and/or products which may also serve as temperature control mechanism.

The invention will now be further described by means of the following non-limiting examples.

EXAMPLES

Example 1

Combined ethylene tetra- and trimerisation reaction using Cr(acetylacetonate)$_3$, (phenyl)$_2$PN($^i$propyl)P(phenyl)$_2$, (o-ethylphenyl)$_2$PN(Me)P(o-ethylphenyl)$_2$ and MAO A solution of 9.4 mg of (phenyl)$_2$PN($^i$propyl)P(phenyl)$_2$ (0.022 mmol) and (tetramerisation ligand) 11.3 mg of (o-ethylphenyl)$_2$PN(Me)P(o-ethylphenyl)$_2$ (0.022 mmol) (trimerisation ligand) in 10 ml of toluene was added to a solution of 7.4 mg Cr(acetylacetonate)$_3$ (0.022 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 40° C. The pressure reactor was charged with ethylene after which the reactor temperature was controlled at 45° C., while the ethylene pressure was maintained at 4500 kPa. The reaction was terminated after 12 min by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid products. These solid products were dried overnight in an oven at 100° C. and then weighed. The mass of total product was 111.66 g. The product distribution of this example is summarised in Table 1.

Example 2

Combined ethylene tetra- and trimerisation reaction using Cr(acetylacetonate)$_3$, (phenyl)$_2$PN($^i$propyl)P(phenyl)$_2$, (o-ethylphenyl)$_2$PN(Me)P(o-ethylphenyl)$_2$ and MAO A solution of 6.4 mg of (phenyl)$_2$PN($^i$propyl)P(phenyl)$_2$ (0.015 mmol). (tetramerisation ligand) and 7.7 mg of (o-ethylphenyl)$_2$PN(Me)P(o-ethylphenyl)$_2$ (0.015 mmol) (trimerisation ligand) in 10 ml of toluene was added to a solution of 7 mg Cr(acetylacetonate)$_3$ (0.02 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 13.5 min, and the procedure of Example 1 above was employed. The product mass was 68.58 g. The product distribution of this example is summarised in Table 1.

Example 3

Combined ethylene tetra- and trimerisation reaction using Cr(acetylacetonate)$_3$, (phenyl)$_2$PN($^i$propyl)P(phenyl)$_2$, (o-ethylphenyl)$_2$PN(Me)P(o-ethylphenyl)$_2$ and MAO A solution of 4.3 mg of (phenyl)$_2$PN($^i$propyl)P(phenyl)$_2$ (0.01 mmol) (tetramerisation ligand) and 10.2 mg of (o-ethylphenyl)$_2$PN(Me)P(o-ethylphenyl)$_2$ (0.02 mmol) (trimerisation ligand) in 10 ml of toluene was added to a solution of 7 mg Cr(acetylacetonate)$_3$ (0.02 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 15 min, and the procedure of Example 1 above was employed. The product mass was 84.35 g. The product distribution of this example is summarised in Table 1.

Example 4

Combined ethylene tetra- and trimerisation reaction using Cr(acetylacetonate)3, (phenyl)$_2$PN($^i$propyl)P(phenyl)$_2$, (o-ethylphenyl)$_2$PN(Me)P(o-ethylphenyl)$_2$ and MAO A solution of 3.2 mg of (phenyl)$_2$PN($^i$propyl)P(phenyl)$_2$ (0.0075 mmol) (tetramerisation ligand) and 11.5 mg of (o-ethylphenyl)$_2$PN(Me)P(o-ethylphenyl)$_2$ (0.0225 mmol) (trimerisation ligand) in 10 ml of toluene was added to a solution of 7 mg Cr(acetylacetonate)$_3$ (0.02 mmol) in 10 ml toluene in a Schlenk vessel.

The mixture was stirred for 5 min at ambient temperature and was then transferred to a 300 ml pressure reactor (autoclave) containing a mixture of toluene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 19 min, and the procedure of Example 1 above was employed. The product mass was 99.05 g. The product distribution of this example is summarised in Table 1.

Example 5

Combined ethylene tetra- and trimerisation reaction using

Cr(acetylacetonate)$_3$, (phenyl)$_2$PN($^i$propyl)P(phenyl)$_2$, (o-ethylphenyl)$_2$PN(Me)P(o-ethylphenyl)$_2$ and MAO A solution of 3.2 mg of (phenyl)$_2$PN($^i$propyl)P(phenyl)$_2$ (0.0075 mmol) (tetramerisation ligand) and 11.5 mg of (o-ethylphenyl)$_2$PN(Me)P(o-ethylphenyl)$_2$ (0.0225 mmol) (trimerisation ligand) in 10 ml of methylcyclohexane was added to a solution of 7 mg Cr(acetylacetonate)$_3$ (0.02 mmol) in 10 ml methylcyclohexane in a Schlenk vessel. The mixture was stirred for 5 min at ambient temperature and was then transferred to a 300 ml pressure reactor (autoclave) containing a mixture of methylcyclohexane (80 ml) and MAO (methylaluminoxane in toluene, 4 mmol) at 40° C. The pressure reactor was charged with ethylene after which the reactor temperature was controlled at 45° C., while the ethylene pressure was maintained at 4500 kPa. The reaction was terminated after 19 min, and the procedure of Example 1 above was employed. The product mass was 91.11 g. The product distribution of this example is summarised in Table 1.

Example 6

Combined ethylene tetra- and trimerisation reaction using Cr(acetylacetonate)$_3$, (phenyl)$_2$PN($^i$propyl)P(phenyl)$_2$, (o-methoxyphenyl)$_2$PN(Me)P(o-methoxyphenyl)$_2$ and MMAO A solution of 4.3 mg of (phenyl)$_2$PN($^i$propyl)P(phenyl)$_2$ (0.01 mmol) (tetramerisation ligand) and 5.1 mg of (o-methoxyphenyl)$_2$PN(Me)P(o-methoxyphenyl)$_2$ (0.01 mmol) (trimerisation ligand) in 5 ml of methylcyclohexane was added to a solution of 7 mg Cr(acetylacetonate)$_3$ (0.02 mmol) in 5 ml methylcyclohexane in a Schlenk vessel. MMAO-3A (modified methylaluminoxane, 5.1 mmol) was added and the mixture was immediately transferred to a 300 ml pressure reactor (autoclave) containing methylcyclohexane (80 ml) at 40° C. The pressure reactor was charged with ethylene after which the reactor temperature was controlled at 45° C., while the ethylene pressure was maintained at 4500 kPa. The reaction was terminated after 7 min, and the procedure of Example 1 above was employed. The product mass was 84.2 g. The product distribution of this example is summarised in Table 1.

Example 7

Combined ethylene tetra- and trimerisation reaction using Cr(acetylacetonate)$_3$, (p-methoxyphenyl)$_2$PN(Me)P(p-methoxyphenyl)$_2$, (o-ethylphenyl)$_2$PN(Me)P(o-ethylphenyl)$_2$ and MMAO A solution of 0.5 mg of (o-ethylphenyl)$_2$PN(Me)P(o-ethylphenyl)$_2$ (trimerisation ligand (0.001 mmol) and 4.7 mg of (p-methoxyphenyl)$_2$PN(Me)P(p-methoxyphenyl)$_2$ (0.009 mmol) (tetramerisation ligand) in 5 ml of methylcyclohexane was added to a solution of 3.5 mg Cr(acetylacetonate)$_3$ (0.01 mmol) in 5 ml methylcyclohexane in a Schlenk vessel. MMAO-3A (modified methylaluminoxane, 1.3 mmol) was added and the mixture was immediately transferred to a 300 ml pressure reactor (autoclave) containing methylcyclohexane (90 ml) at 40° C. The pressure reactor was charged with ethylene after which the reactor temperature was controlled at 45° C., while the ethylene pressure was maintained at 4500 kPa. The reaction was terminated after 23 min, and the procedure of Example 1 above was employed. The product mass was 47.9 g. The product distribution of this example is summarised in Table 1.

Example 8

Combined ethylene tetra- and trimerisation reaction using

Cr(acetylacetonate)$_3$, Ph$_2$PN(Me)N(Me)PPh$_2$, (o-ethylphenyl)$_2$PN(Me)P(o-ethylphenyl)$_2$ and MMAO A solution of 3.9 mg of Ph$_2$PN(Me)N(Me)PPh$_2$ (0.009 mmol) (tetramerisation ligand) and 0.5 mg of (o-ethylphenyl)$_2$ PN(Me)P(o-ethylphenyl)$_2$ (0.001 mmol) (trimerisation ligand) in 5 ml of methylcyclohexane was added to a solution of 3.5 mg Cr(acetylacetonate)$_3$ (0.01 mmol) in 10 ml methylcyclohexane in a Schlenk vessel. MMAO-3A (modified methylaluminoxane, 2.5 mmol) was added and the mixture was immediately transferred to a 300 ml pressure reactor (autoclave) containing methylcyclohexane (80 ml) at 40° C. The pressure reactor was charged with ethylene after which the reactor temperature was controlled at 45° C., while the ethylene pressure was maintained at 4500 kPa. The reaction was terminated after 5 min, and the procedure of Example 1 above was employed. The product mass was 52.47 g. The product distribution of this example is summarised in Table 1.

Example 9

Combined ethylene tetra- and oligomerisation reaction using Cr(acetylacetonate)$_3$, (phenyl)$_2$PN($^i$propyl)P(phenyl)$_2$, Fe-bisiminopyridyl (1) and MMAO A solution of 6.5 mg of (phenyl)$_2$PN($^i$propyl)P(phenyl)$_2$ (0.016 mmol) (tetramerisation ligand) and 5.25 mg Cr(acetylacetonate)$_3$ (0.015 mmol) in 5 ml toluene was added to a suspension of 1.64 mg (0.0035 mmol) of (1) (ethylene oligomerisation catalyst[1a]) in 5 ml toluene in a Schlenk vessel. The mixture was transferred to a 300 ml pressure reactor (autoclave) containing a mixture of toluene (90 ml) and MAO (methylaluminoxane in toluene, 9.5 mmol) at 40° C. The pressure reactor was charged with ethylene after which the reactor temperature was controlled at 45° C., while the ethylene pressure was maintained at 3000 kPa. The reaction was terminated after 30 min, and the procedure of Example 1 above was employed. The product mass was 34.6 g. The product distribution of this example is summarised in Table 2.

1a) B. L. Small, M. Brookhart, J. Am. Chem. Soc., 1998, 120, 7143. 1b) G. J. P. Britovsek, S. Mastroianni, G. A. Solan, S. P. D. Baugh, C. Redshaw, V. C. Gibson, A. J. P. White, D. J. Williams and M. R. J. Elsegood, Chemistry—A European Journal, 2000, 6, 2221.

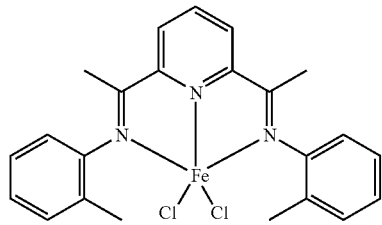

(1)

Example 10

Ethylene oligomerisation reaction using Fe-bisiminopyridyl (1) and MMAO (comparative example)

A suspension of 2.34 mg (0.005 mmol) of (1) (see example 9, ethylene oligomerisation catalyst[1]) in 10 ml toluene was added to a 300 ml pressure reactor (autoclave) containing a mixture of toluene (90 ml) and MAO (methylaluminoxane in toluene, 2.5 mmol) at 90° C. The pressure reactor was charged with ethylene after which the reactor temperature was controlled at 90° C., while the ethylene pressure was maintained at 3000 kPa. The reaction was terminated after 6 min, and the procedure of Example 1 above was employed. The product mass was 109.4 g. The product distribution and the k-value for the Schulz-Flory distribution of this example are summarised in Table 2.

TABLE 1

Combined Tri- and Tetramerisation

| Example | activity g/g Cr | C-6 % | 1-hex. % | C-8 % | 1-oct. % |
|---|---|---|---|---|---|
| 1 | 97600 | 43 | 87.6 | 52.8 | 98.9 |
| 2 | 65800 | 38.7 | 98.3 | 51.4 | 98.8 |
| 3 | 81000 | 52.9 | 94.2 | 38.2 | 98.9 |
| 4 | 95100 | 58.5 | 93.1 | 36 | 98.9 |
| 5 | 87500 | 62.2 | 96.5 | 25.7 | 99 |
| 6 | 81000 | 47.3 | 93.9 | 40.5 | 98.9 |
| 7 | 92100 | 78.7* | 96.4 | 12.2* | 93.2 |
| 8 | 100900 | 56.9 | 94.1 | 34.4 | 99.2 |

*Liquid fraction (i.o.w. selectivities excluding the polymeric side products)
Percentages are expressed as weight % (of total product).

Percentages are expressed as weight % (of total product)

TABLE 2

Combined Oligomerisation and Tetramerisation

| Example | activity g/g metal | C-6 % | 1-hex. % | C-8 % | 1-oct. % | C-10 % | C-12 % | C-14 % | k-value |
|---|---|---|---|---|---|---|---|---|---|
| 9 | 35300 | 18.0 | 82.0 | 33.3 | 96.0 | 7.0 | 4.9 | 3.5 | n/a |
| 10 | 391900 | 10.6 | 98.0 | 9.5 | 97.0 | 11.2 | 9.2 | 5.7 | 0.73 |

Percentages are expressed as weight % (of total product).

The invention claimed is:

1. An oligomerisation process comprising contacting at least one olefinic compound in the form of an olefin or a compound including an olefinic moiety with at least two different catalysts, including a tetramerisation catalyst and a further oligomerisation catalyst to produce an oligomeric product, which includes a mixture of at least one tetramer olefin and at least one other oligomer, wherein the tetramerisation catalyst comprises a combination of i) a source of a transition metal which transition metal is Cr; and
ii) a ligating compound of the formula $(R^1)_m X^1(Y) X^2(R^2)_n$ wherein: $X^1$ and $X^2$ are independently selected from the group consisting of N, P, As, Sb, Bi, O, S and Se; Y is a linking group between $X^1$ and $X^2$; provided Y excludes $(CH_2)_x Z(CH_2)_y$, where Z is —P($R^8$)—, —N($R^8$)—, —As($R^8$)—, —Sb($R^8$)— or —S—, and x and y are individually 1-15, and wherein $R^8$ is hydrogen or a halogen or a nitro group or a hydrocarbyl or a substituted hydrocarbyl group; m and n are independently 0, 1 or a larger integer; and $R^1$ and $R^2$ are independently hydrogen, a hydrocarbyl group, or a heterohydrocarbyl group, and $R^1$ is the same or different when m>1, and $R^2$ is the same or different when n>1, provided that:

(a) if two or more of $R^1$ and $R^2$ are aromatic with a ring atom of the aromatic ring structure bound to either $X^1$ of $X^2$, not more than two of said aromatic $R^1$ and $R^2$ have a substituent as a non-ring atom bound to a ring atom of the aromatic ring structure adjacent to the ring atom bound to $X^1$ or $X^2$; and
(b) none of $R^1$ and $R^2$ are aromatic with a ring atom of the aromatic ring structure bound to either $X^1$ and $X^2$ and with a polar substituent as a non-ring atom bound to a ring atom of the aromatic ring structure adjacent to the ring atom bound to $X^1$ or $X^2$;

and wherein the further oligomerisation catalyst is a catalyst comprising the combination of iii) a source of transition metal; and
iv) a ligating compound of the formula $(R')_{n'} A-B-C(R'')_{m'}$ wherein:
A and C are independently selected from the group consisting of N, P, As, Sb, Bi, O, S and Se;
B is a linking group between A and C;
m' and n' are independently 0, 1 or larger integer;
R' and R" are independently hydrogen, a hydrocarbyl group or a heterohydrocarbyl group;
and R' is the same or different when n'>1, and R" is the same or different when m'>1 and
wherein the oligomeric product of the process contains from 9.5 wt % to 52.8 wt % of the tetramer olefin.

2. The process of claim 1 wherein the source of Cr is selected from the group of compounds consisting of an inorganic salt, an organic salt, a coordination compound and an organometallic complex.

3. The process of claim 2 wherein the source of Cr is selected from the group consisting of chromium trichloride tris-tetrahydrofuran complex; (benzene)tricarbonyl chromium; chromium (III) octanoate; chromium hexacarbonyl; chromium (III) acetylacetonate and chromium (III) 2-ethyl hexanoate.

4. The process of any one of claims 1-3 wherein the ligating compound ii) is of the formula

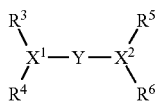

wherein $X^1$ and $X^2$ are independently selected from the group consisting of N, P, As, Sb and Bi; and $R^3$ to $R^6$ are the same or different and are each independently a hydrocarbyl group or a heterohydrocarbyl group, provided that (a) if two or more of $R^3$ to $R^6$ are aromatic with a ring atom of the aromatic ring structure bound to either $X^1$ of $X^2$ not more than two of said aromatic $R^3$ to $R^6$ have a substituent as a non-ring atom bound to a ring atom of the aromatic ring structure adjacent to the ring atom bound to $X^1$ or $X^2$; and (b) none of $R^3$ to $R^6$ are aromatic with a ring atom of the aromatic ring structure bound to $X^1$ and $X^2$ with a polar substituent as a non-ring atom bound to a ring atom of the aromatic ring structure adjacent to the ring atom bound to $X^1$ or $X^2$.

5. The process of claim 4 wherein $X^1$ and $X^2$ are the same.

6. The process of claim 5 wherein both $X^1$ and $X^2$ are P.

7. The process of claim 4 wherein $R^3$ to $R^6$ are the same or different and each is a hydrocarbyl group, or a heterohydrocarbyl group which contains no substituent or contains a non-polar substitutent.

8. The process of claim 7 wherein each of $R^3$ to $R^6$ does not have any polar substituent.

9. The process of claim 8 wherein at least two of $R^3$ to $R^6$ are aromatic with a ring atom of the aromatic ring structure bound to $X^1$ or $X^2$, but not more than two of said aromatic $R^3$ to $R^6$ have a non-polar substitutent as a non-ring atom bound to a ring atom of the aromatic ring structure adjacent to the ring atom bound to $X^1$ or $X^2$.

10. The process of claim 9 wherein all of $R^3$ to $R^6$ are aromatic and none of the aromatic $R^3$ to $R^6$ have a non-polar substituent as a non-ring atom bound to a ring atom of the aromatic ring structure adjacent to the ring atom bound to $X^1$ or $X^2$.

11. The process of claim 4 wherein $R^3$ to $R^6$ are the same or different and each is a hydrocarbyl group, or a heterohydrocarbyl group, provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$.

12. The process of claim 4 wherein Y is selected from the group consisting of an organic linking group; an inorganic linking group; methylene; dimethylmethylene; 1,2-ethane; 1,2-ethene; 1,1-cyclopropane; 1,1-cyclobutane; 1,1-cyclohexane; 1,1-cyclopentane; 1,2-cyclopentane; 1,2-cyclohexane; 1,2-phenylene; 1,8-naphthyl; 9,10-phenanthrene; 4,5-phenanthrene; 1,3-propane; 1,2-catechol; 1,2-dialkylhydrazine; —B($R^7$)—; —Si($R^7$)$_2$—; —P($R^7$)— and —N($R^7$)— where $R^7$ is hydrogen, a hydrocarbyl or a heterohydrocarbyl group or halogen.

13. The process of claim 12 wherein Y is —N($R^7$)— and $R^7$ is a hydrocarbyl or a heterohydrocarbyl group.

14. The process of claim 1 wherein the catalyst includes one or more activators.

15. The process of claim 14 wherein the one or more activators are one or more organoaluminium compounds.

16. The process of claim 1 wherein the oligomerisation catalyst is a trimerisation catalyst.

17. The process of claim 1 wherein the source of transition metal of the tetramerisation catalyst and the source of transition metal of the further oligomerisation catalyst is the same source.

18. The process of claim 17 wherein both the tetramerisation catalyst and the further oligomerisation catalyst are prepared in the same medium and in situ, the preparation being carried out by combining:

i) a source of transition metal for both the tetramerisation catalyst and the further oligomerisation catalyst;
ii) a ligating compound for the tetramerisation catalyst;
iii) a different ligating compound for the oligomerisation catalyst; and
iv) optionally an activator.

19. The process of claim 1 wherein the at least one olefinic compound comprises a single olefinic compound.

20. The process of claim 19 wherein the single olefinic compound is ethene.

21. The process of claim 1 which is carried out in an inert solvent.

22. An oligomeric product produced by the process of claim 1.

23. An oligomerisation catalyst comprising the combination of:

i) a source of Cr for both a tetramerisation catalyst and a trimerisation catalyst;
ii) a ligating compound for a tetramerisation catalyst of the formula

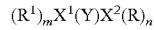

$(R^1)_m X^1 (Y) X^2 (R^2)_n$ wherein: $X^1$ and $X^2$ are independently selected from the group consisting of N, P, As, Sb, Bi, O, S and Se;
Y is a linking group between $X^1$ and $X^2$; provided Y excludes $(CH_2)_x Z (CH_2)_y$, where Z is —P($R^8$)—, —N($R^8$)—, —As($R^8$)—, —Sb($R^8$)— or —S—, and x and y are individually 1-15, and wherein $R^8$ is hydrogen or a halogen or a nitro group or a hydrocarbyl or a substituted hydrocarbyl group; m and n are independently 0, 1 or a larger integer; and $R^1$ and $R^2$ are independently hydrogen, a hydrocarbyl group, or a heterohydrocarbyl group, and $R^1$ is the same or different when m>1, and $R^2$ is the same or different when n>1, provided that:

(a) if two or more of $R^1$ and $R^2$ are aromatic with a ring atom of the aromatic ring structure bound to either $X^1$ of $X^2$, not more than two of said aromatic $R^1$ and $R^2$ have a substituent as a non-ring atom bound to a ring atom of the aromatic ring structure adjacent to the ring atom bound to $X^1$ or $X^2$; and (b) none of $R^1$ and $R^2$ are aromatic with a ring atom of the aromatic ring structure bound to either $X^1$ and $X^2$ and with a polar substituent as a non-ring atom bound to a ring atom of the aromatic ring structure adjacent to the ring atom bound to $X^1$ or $X^2$;

iii) a different ligating compound for a trimerisation catalyst; and
iv) optionally an activator.

24. The process of claim 12 wherein the organic linking group is a hydrocarbyl, a substituted hydrocarbyl, a heterohydrocarbyl or a substituted heterohydrocarbyl group.

25. The process of claim 12 wherein the inorganic linking group is a single atom link bound to both $X^1$ and $X^2$.

26. The process of claim 1 wherein the at least one tetramer olefin is 1-octene.

* * * * *